US00PP13469P3

(12) United States Plant Patent
Larson et al.

(10) Patent No.: US PP13,469 P3
(45) Date of Patent: Jan. 14, 2003

(54) STRAWBERRY PLANT NAMED 'VENTANA'

(75) Inventors: Kirk D. Larson, Irvine, CA (US); Douglas V. Shaw, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/776,754

(22) Filed: Feb. 6, 2001

(65) Prior Publication Data

US 2002/0152523 P1 Oct. 17, 2002

(51) Int. Cl.[7] ..... A01H 5/00

(52) U.S. Cl. ..... Plt./208

(58) Field of Search ..... Plt./208

*Primary Examiner*—Bruce R. Campell
*Assistant Examiner*—Michelle Kizilkaya
(74) *Attorney, Agent, or Firm*—Burns, Doane, Swecker & Mathis, LLP

(57) ABSTRACT

A new and distinct short-day strawberry cultivar is provided. Attractive pointed symmetrical-conic bright light red fruit of good quality typically is formed in a good yield. The fruit flavor is good and the fraction of non-marketable fruit tends to be low. The growth habit is large, erect, and open. Flat to very concave leaflets having semi-pointed to pointed serrations are formed.

5 Drawing Sheets

BOTANICAL/COMMERCIAL CLASSIFICATION

*Fragaria×ananassa Duch.*/Strawberry Plant.

VARIETAL DENOMINATION cv. 'Ventana'.

FIELD OF THE INVENTION

A new and distinctive short-day type strawberry cultivar designated 'Ventana' is provided that resulted from a cross performed in 1996 between advanced selections Cal 93.170-606 (non-patented in the United States) and Cal 92.35-601 (non-patented in the United States). The cultivar is botanically identified as *Fragaria×ananassa Duch.* The parentage of the new cultivar can be summarized as follows:

Cal 93.170-606×Cal 92.35-601.

'Ventana' was first fruited at the University of California, South Coast Research and Extension Center near Irvine, Calif., U.S.A., in 1997, where it was selected, was originally designated Cal 96.42-601, and was propagated asexually by runners. The characteristics of the new cultivar have been found to be fully transmissible by such asexual propagation. Following selection and during testing the plant was designated 'C216', and subsequently has been named 'Ventana' for introduction. Asexual propagules from this original source have been tested in the Watsonville Strawberry Research Facility, the South Coast Research and Extension Center of the University of California, and to a limited extent in grower test fields starting in 1998.

The new 'Ventana' cultivar can be readily distinguished from its ancestors. For instance, the new cultivar displays different fruit appearance and fruit quality traits. The red coloration of the 'Ventana' fruit is intermediate that of its parents and is even throughout the fruit surface with a very high gloss. The fruit of Cal 93.170-606 is very dark and the external coloration frequently is uneven and mottled across the surface. The fruit of Cal 92.35-601 is light colored, frequently bears a white shoulder, and is generally lacking a shine. The 'Ventana' fruit bears a flattened conic configuration with rather angular straight sides, a solid core, and seeds that are commonly even with the fruit surface. The fruit of Cal 97.170-606 commonly bears indented seeds, and a shortened conic or wedge shape. The fruit of Cal 92.35-601 commonly bears partially extruded seeds, has a hollow care, and has edges that curve to a point.

It was found that the new cultivar of the present invention exhibits the following combination of characteristics:

(a) Exhibits a large, erect and open growth habit, (b) Typically forms attractive pointed symmetrical-conic bright light red fruit of good quality and in a good yield, and (c) Forms flat to very concave leaflets having semi-pointed to pointed serrations.

BRIEF DESCRIPTION OF THE PHOTOGRAPHS

The depicted plants and plant parts were grown in California, U.S.A. Such runner plants were approximately seven to nine months of age.

Figure 1:
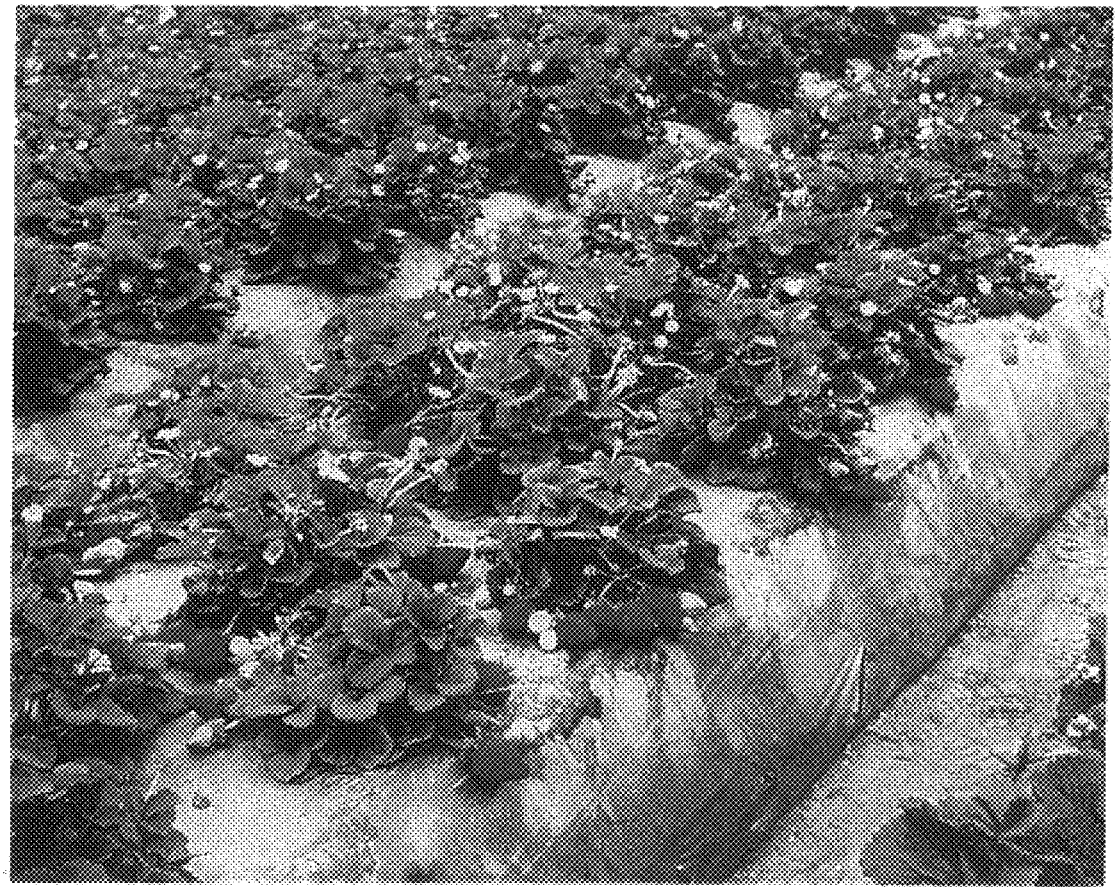
Figure 2:
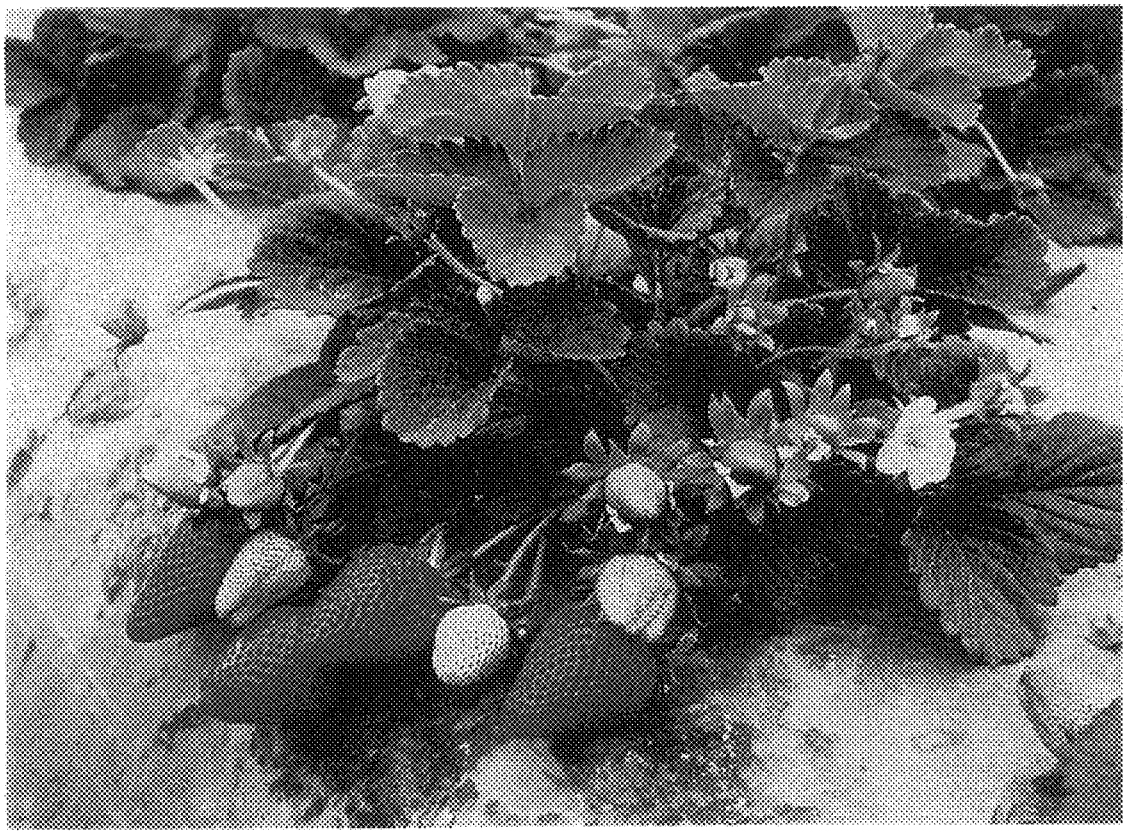
Figure 3:
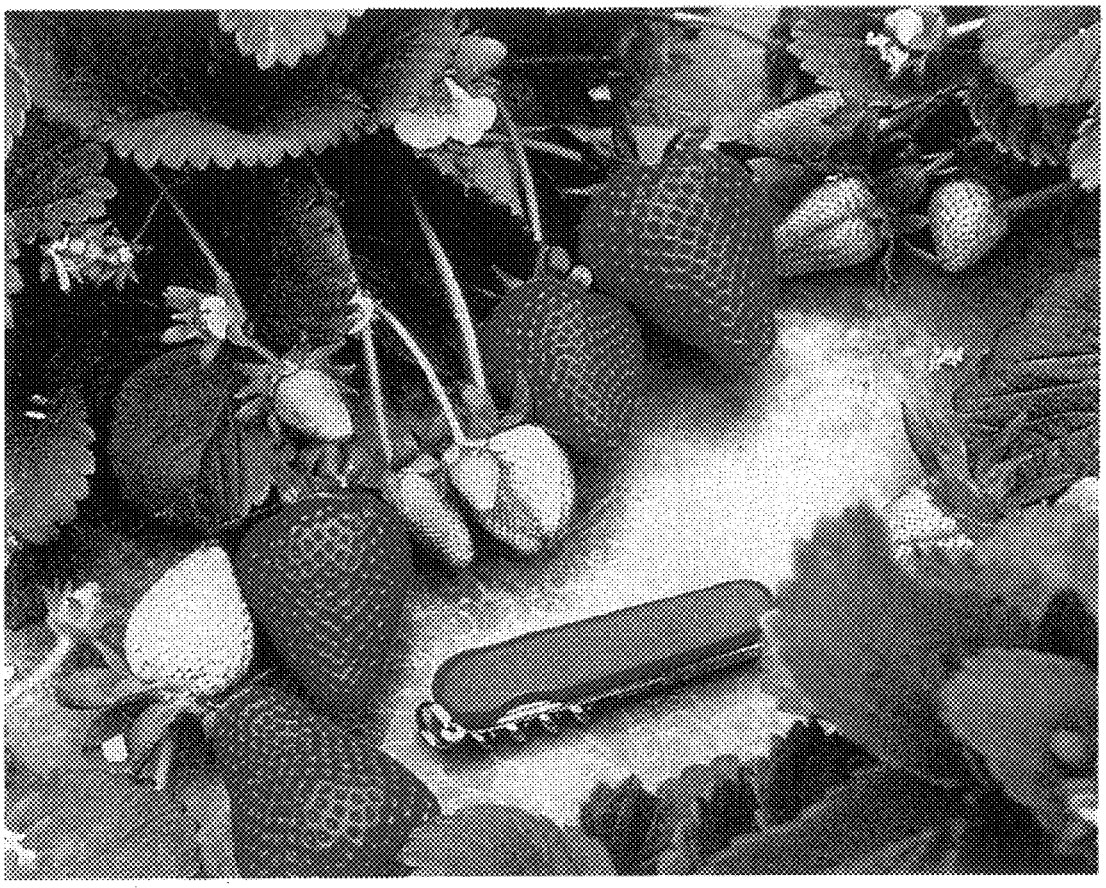
Figure 4:
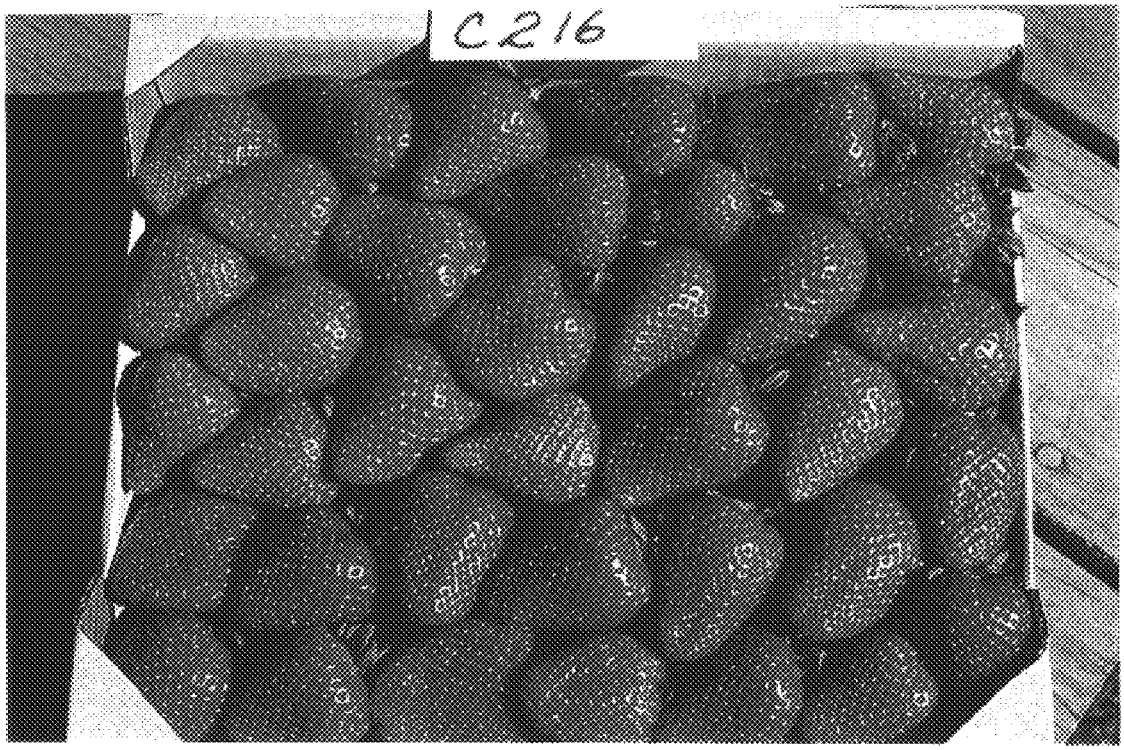
Figure 5:
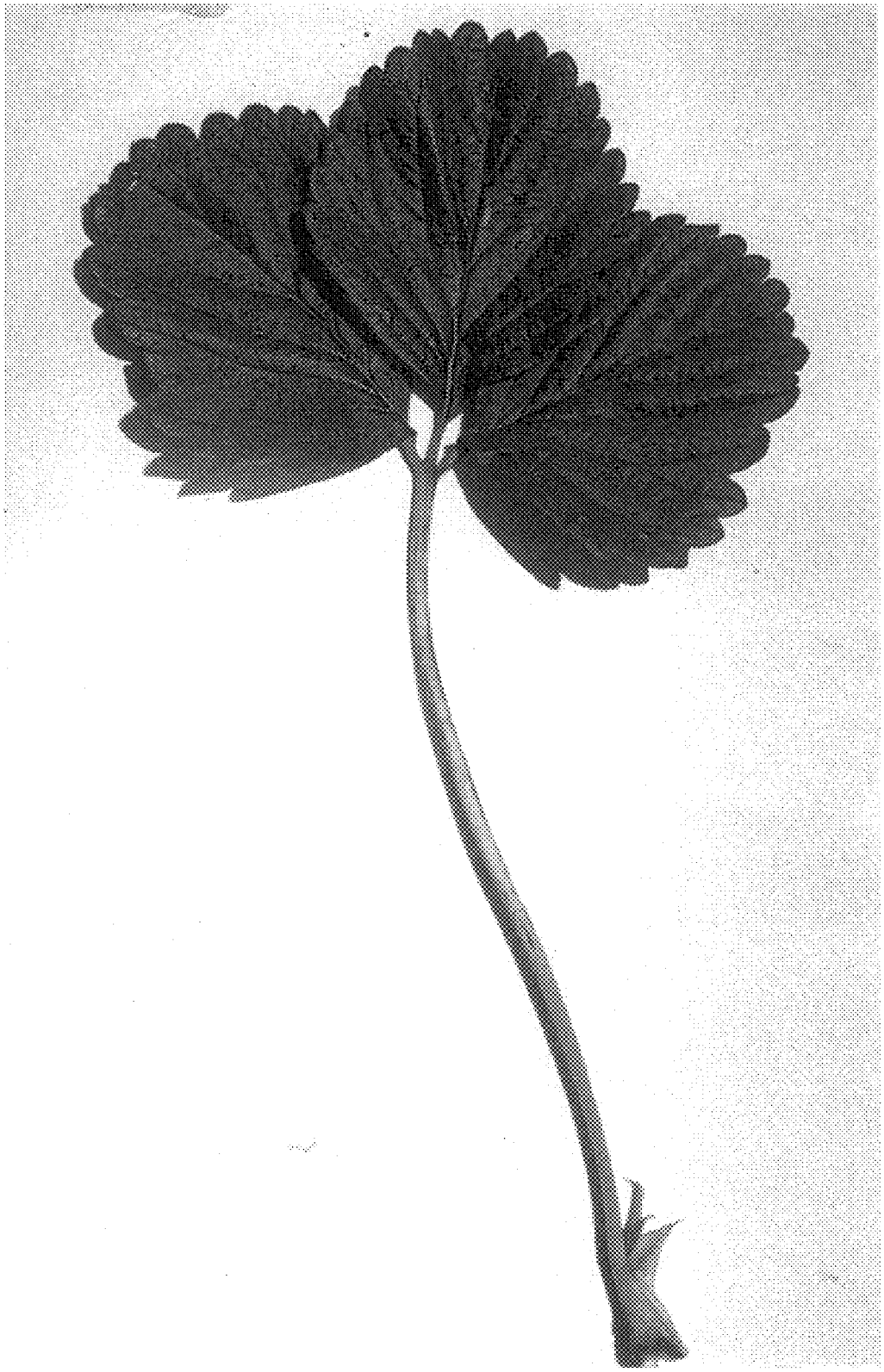

FIG. 1—shows rows of typical fruiting plants during early to mid-March, 2000, in Irvine;

FIG. 2—shows a representative individual flowering and fruiting plant during early March, 2000, at Irvine wherein the erect and open growth habit is depicted;

FIG. 3—shows a closer view of representative immature and mature fruit present on the plants;

FIG. 4—shows a half-crate of representative fruit during mid-May, 2000, grown in Watsonville;

FIG. 5—shows a typical mature leaf during late spring.

DETAILED DESCRIPTION

The plants described herein were grown while using standard annual hillculture strawberry production practices as described in "Strawberry Production in California" by N. C. Welch, University of California Div. Agr. Nat. Resources Publication No. 2959 (1990). This included preplant fumigation, controlled release fertilization, and cover with clear polyethylene mulch prior to planting.

'Ventana' as other short-day strawberry cultivars produces fruit over an extended period when treated appropriately in arid, subtropical climates. The production pattern for 'Ventana' is similar to that of the 'Camarosa' cultivar (U.S. Plant Pat. No. 8,708). It initiates fruiting at approximately the same time as the 'Camarosa' cultivar and produces greater quantities of early-season fruit with most cultural treatments. 'Ventana' will be of special interest for winter plantings where the 'Camarosa' cultivar has been successful, and in summer plantings where the 'Pajaro' cultivar (U.S. Plant Pat. No. 4,538) and the 'Chandler' cultivar (U.S. Plant Pat. No. 5,262) have been successful.

Plants and Foliage

Fruiting plants of 'Ventana' are large and vigorous, similar to those of the 'Camarosa' cultivar, but more open than plants of the 'Camarosa' cultivar. 'Ventana' plants are larger and somewhat less erect than plants of the 'Gaviota' cultivar (U.S. Plant Pat. No. 10,461). Comparative statistics for foliar characters near mid-season are given for the three cultivars in Table 1 that follows. Individual leaflets for 'Ventana' are similar to those of the 'Gaviota' cultivar, and are somewhat more rounded than the leaflets of the 'Camarosa' cultivar. The leaves (including petioles) are longer and more narrow than those of the 'Gaviota' cultivar. The leaves are similar in size to those of the 'Camarosa' cultivar. The petioles are similar in thickness to those of the 'Camarosa' cultivar. 'Ventana' has a more concave leaf form than the 'Gaviota' and 'Camarosa' cultivars, and has more serrations and lighter leaf pubescence than the comparison cultivars.

TABLE 1

| | Cultivar | | |
|---|---|---|---|
| Foliar Character | 'Camarosa' | 'Gaviota' | 'Ventana' |
| Mid-Tier Leaflet Length (mm) | | | |
| mean | 91 | 95 | 93 |
| range | 80 to 100 | 83 to 109 | 75 to 115 |
| Width (mm) | | | |
| mean | 83 | 95 | 92 |
| range | 68 to 104 | 71 to 105 | 82 to 108 |
| Mid-Tier Leaf Length (mm) | | | |
| mean | 313 | 254 | 296 |
| range | 256 to 426 | 201 to 314 | 244 to 346 |
| Width (mm) | | | |
| mean | 161 | 182 | 174 |
| range | 130 to 183 | 146 to 205 | 134 to 205 |
| Number of Leaflets/Leaf | 3 | 3 | 3 |
| Leaf Convexity | flat-convex, most are slightly concave | most are concave, some flat | flat to very concave |
| Serrations | | | |
| number | few to moderate | few to moderate | moderate pointed |
| shape | rounded, some semi-pointed | rounded to semi-pointed | to semi-pointed |
| Leaf Pubescence | light–moderate | light–moderate | light |

TABLE 1-continued

| | Cultivar | | |
|---|---|---|---|
| Foliar Character | 'Camarosa' | 'Gaviota' | 'Ventana' |
| Petiole Pubescence | | | |
| density | moderate to heavy perpendicular to acropetal | heavy perpendicular | moderate perpendicular to slightly acropetal |
| direction | | | |

The adaxial (upper) surfaces of leaves of 'Ventana' are lighter in color than those of the 'Gaviota' cultivar and similar to those of the 'Camarosa' cultivar although they occasionally are more yellow. See Table 2 that follows.

TABLE 2

| | | Cultivar | | |
|---|---|---|---|---|
| | | 'Camarosa' | 'Gaviota' | 'Ventana' |
| Leaf Color (CIELAB)* | | | | |
| Adaxial | | | | |
| L* | mean | 32.3 | 29.0 | 32.9 |
| | range | 30.8 to 34.6 | 27.4 to 30.0 | 31.6 to 34.8 |
| a* | mean | −7.0 | −7.0 | −7.9 |
| | range | −4.8 to −8.2 | −6.1 to −7.7 | −7.0 to −9.4 |
| b* | mean | 14.0 | 11.5 | 15.8 |
| | range | 9.4 to 18.4 | 9.7 to 13.7 | 13.8 to 18.3 |
| Munsell | | 5GY 4/3 | 5GY 4/3 | 10Y 4/3 |
| Adaxial | | | | |
| L* | mean | 46.1 | 47.5 | 48.1 |
| | range | 43.9 to 49.2 | 46.4 to 48.7 | 46.1 to 49.7 |
| a* | mean | −7.6 | −7.6 | −7.5 |
| | range | −6.8 to −8.0 | −6.7 to −8.5 | −6.7 to −8.0 |
| b* | mean | 21.8 | 20.4 | 19.0 |
| | range | 20.1 to 25.0 | 17.2 to 24.5 | 17.5 to 23.3 |
| Munsell | | 2.5GY 5/5 | 2.5GY 5/5 | 2.5GY 4/3 |

*CIELAB is the abbreviation of the international color system known as "Commission Internationale De L'Eclairage" 1978. For recommendations concerning uniform color spaces, color difference equations, and psychometric color terms see Supplement No. 2 of CIE Publication No. 15, Paris.

Isozymes in Leaf Extracts

'Ventana' has been classified for three isozyme systems using Starch Gel Electrophoresis: Phosophoglucoisomerase (PGI), Leucine Aminopeptidase (LAP), and Phosphoglucomutase (PGM). It is distinguishable from the 'Gaviota' and 'Camarosa' cultivars using this methodology. See Table 3 that follows.

TABLE 3

| | Cultivar | | |
|---|---|---|---|
| Locus | 'Camarosa' | 'Gaviota' | 'Ventana' |
| PGI | A2 | A2 | A1 |
| LAP | B3 | B3 | B1 |
| PGM | C1 | C1 | C2 |

For electrophoretic procedures see: *J. Amer. Soc. Hort. Sci.* 106:684 to 687.

Disease and Pest Reactions

'Ventana' is moderately susceptible to common leaf spot (*Ramularia tulasnei*) and Verticillium wilt (*Verticillium dahliae*). It is quite resistant to Phytophthora crown rot (*Phytophthora cactorum*), and relatively resistant to powdery mildew (*Sphaerotheca macularis*). When treated properly, it has tolerance to two-spotted spidermites (*Tetranychus urticae*) equal or greater to that of the 'Gaviota' and 'Camarosa' cultivars. 'Ventana' is tolerant to strawberry viruses encountered in California.

Flowering, Fruiting, Fruit and Production Characteristics

Comparative statistics for flower and fruit characters near mid-season are given for 'Camarosa', 'Gaviota' and 'Ventana' in Table 4 that follows. The primary flowers for 'Ventana' are similar in size to those of the 'Gaviota' and 'Camarosa' cultivars although somewhat smaller in late spring. The sepals are somewhat smaller than those of the 'Gaviota' or 'Camarosa' cultivars. The calyx for 'Ventana' varies from even with the fruit shoulder to slightly necked, and each primary flower has 6 to 8 petals. The fruit shape for 'Ventana' is typically symmetrical conic, and is readily distinguishable from that of the 'Camarosa' cultivar that is shortened flat conic. 'Ventana' has a greater proportion of symmetrical fruit than the 'Gaviota' cultivar. Achenes vary from yellow to dark red, and are substantially even with the fruit surface or slightly indented.

TABLE 4

| | Cultivar | | |
|---|---|---|---|
| Character | 'Camarosa' | 'Gaviota' | 'Ventana' |
| Number of Petals | | | |
| mean | 6.3 | 5.9 | 6.7 |
| range | 5 to 8 | 5 to 8 | 6 to 8 |
| Flower Position (relative to foliage) | mostly even some exposed | exposed | even to exposed |
| Calyx Diam. (mm) | | | |
| mean | 48.1 | 41.7 | 35.1 |
| range | 32 to 58 | 30 to 58 | 31 to 45 |
| Corolla Diam. (mm) | | | |
| mean | 35.6 | 37.9 | 33.4 |
| range | 30 to 47 | 32 to 48 | 31 to 37 |
| Fruit Shape length/width | | | |
| ratio | 1.13 | 1.22 | 1.19 |
| range | 0.61 to 1.51 | 1.02 to 1.45 | 1.10 to 1.31 |
| subjective | Short flat conic | mostly rounded conic, some flat conic | Symmetrical conic |
| Calyx Position | even to slightly necked | even to slightly indented | even to slightly necked |
| Seed Position | even to slightly indented | even | even to extruded |

External and internal fruit color for 'Ventana' is lighter than that of the 'Camarosa' and 'Gaviota' cultivars, and is substantially brighter in coloration. See Table 5 that follows where CIELAB fruit color information is presented.

TABLE 5

| | | Cultivar | | |
|---|---|---|---|---|
| | | 'Camarosa' | 'Gaviota' | 'Ventana' |
| External | | | | |
| L* | mean | 23.3 | 22.4 | 23.8 |
| | range | 20.7 to 27.0 | 20.3 to 24.5 | 17.5 to 28.4 |
| a* | mean | 26.6 | 28.2 | 33.4 |
| | range | 21.6 to 29.5 | 25.3 to 31.4 | 27.9 to 38.0 |
| b* | mean | 12.8 | 14.8 | 19.4 |
| | range | 9.9 to 14.6 | 12.0 to 17.7 | 13.3 to 28.2 |
| Munsell | | 2.5R 3/7 | 5R 3/7 | 5R 4/12 |
| Internal | | | | |
| L* | mean | 44.0 | 48.1 | 50.7 |
| | range | 40.7 to 46.9 | 44.3 to 53.9 | 46.2 to 60.0 |
| a* | mean | 41.4 | 37.2 | 33.2 |
| | range | 35.0 to 45.1 | 26.1 to 41.3 | 21.8 to 36.8 |
| b* | mean | 29.9 | 28.6 | 24.5 |
| | range | 24.1 to 35.3 | 19.9 to 32.6 | 16.4 to 27.5 |
| Munsell | | 5R 4/12 | 5R 5/13 | 5R 5/13 |

Performance

'Ventana' has been tested under a variety of cultural regimes, and optimal performance is obtained when nursery treatments and nutritional programs similar to those used with the 'Camarosa' cultivar are employed. When following appropriate planting regimes, 'Ventana' has similar fruit size and produces greater individual-plant yields than the 'Gaviota' or 'Camarosa' cultivars. In general, 'Ventana' is well adapted to very early season planting. 'Ventana' is earlier in its production pattern than the 'Gaviota' cultivar and similar to that of the 'Camarosa' cultivar, but with substantially greater production of early-season fruit (with conventional winter planting in southern or central California). Commercial appearance ratings have been better than those of the 'Camarosa' cultivar and trials conducted in Santa Maria, Calif., U.S.A. in 1999 to 2000 have indicated that the fraction of non-marketable fruit that is less than one-half that produced by the 'Camarosa' cultivar. Fruit for 'Ventana' is slightly firmer than fruit of the 'Gaviota' cultivar, and slightly less firm than that of the 'Camarosa' cultivar. Subjectively, 'Ventana' has very good flavor. The fruit will be outstanding for both fresh market and processing, and will be useful for home garden purposes. See the comparative data presented in Table 6 that follows. There information is provided for plants that were evaluated during 1999 and 2000 at the South Coast Research and Extension Center of the University of California near Irvine, Calif., U.S.A. Such plants had been asexually reproduced by the use of runners in Macdoel, Calif., U.S.A., were harvested on October $1^{st}$ to $3^{rd}$, and were transplanted approximately 2 to 4 days after harvest. The test planting consisted of 64 inch four-row beds, 21,780 plants/acre. Harvest was initiated in late December and continued through the last week of June.

TABLE 6

| Cultivar | Early Yield* (g/plant) | Yield (g/plant) | Appearance Score | Fruit Size (g/fruit) | Firmness |
|---|---|---|---|---|---|
| 'Camarosa' | 254 | 1,271 | 3.0 | 29.3 | 3.2 |
| 'Gaviota' | 179 | 764 | 2.8 | 29.5 | 2.4 |
| 'Ventana' | 277 | 1,511 | 3.3 | 31.1 | 3.5 |

*Marketable yield to March 10.

'Ventana' has not been observed under all possible environmental conditions to date. Accordingly, it is possible that the phenotype may vary somewhat with variations in the environment.

We claim:

1. A new and distinct short-day strawberry plant cultivar that exhibits the following combination of characteristics:

(a) Exhibits a large, erect and open growth habit, (b) Typically forms attractive pointed symmetrical-conic bright light red fruit of good quality and good yield, and (c) Forms flat to very concave leaflets having semi-pointed to pointed serrations;

substantially as illustrated and described.

* * * * *